(12) United States Patent
Bombardelli

(10) Patent No.: US 7,910,139 B2
(45) Date of Patent: Mar. 22, 2011

(54) COMPOSITIONS FOR THE TREATMENT OF AFFECTIONS OF THE ORAL CAVITY AND UPPER RESPIRATORY TRACT

(75) Inventor: Ezio Bombardelli, Gropello Cairoli (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/580,190

(22) PCT Filed: Nov. 4, 2004

(86) PCT No.: PCT/EP2004/012472
§ 371 (c)(1),
(2), (4) Date: May 23, 2006

(87) PCT Pub. No.: WO2005/053719
PCT Pub. Date: Jun. 16, 2005

(65) Prior Publication Data
US 2007/0104661 A1    May 10, 2007

(30) Foreign Application Priority Data

Nov. 24, 2003   (IT) .............................. MI2003A2287

(51) Int. Cl.
| | | |
|---|---|---|
| *A61K 36/00* | (2006.01) | |
| *A61K 36/87* | (2006.01) | |
| *A61K 36/82* | (2006.01) | |
| *A61K 36/45* | (2006.01) | |
| *A61K 36/38* | (2006.01) | |

(52) U.S. Cl. ........ 424/725; 424/766; 424/729; 424/732; 424/730; 424/774; 424/777; 424/58

(58) Field of Classification Search ......................... None
See application file for complete search history.

(56) References Cited

U.S. PATENT DOCUMENTS

| | | | |
|---|---|---|---|
| 4,503,256 A | | 3/1985 | Fourie et al. |
| 5,370,863 A | * | 12/1994 | Barney et al. .................... 424/49 |
| 5,474,774 A | * | 12/1995 | Walker et al. .................. 424/732 |
| 5,650,432 A | | 7/1997 | Walker et al. |
| 5,895,652 A | * | 4/1999 | Giampapa ................ 424/195.17 |
| 5,955,102 A | * | 9/1999 | Gorenbein et al. ............. 424/451 |
| 6,224,906 B1 | * | 5/2001 | Ghosal .......................... 424/464 |
| 6,284,289 B1 | * | 9/2001 | Van den Berghe ............ 424/746 |
| 6,379,720 B1 | * | 4/2002 | Cooper et al. ................. 424/778 |
| 6,576,269 B1 | * | 6/2003 | Korneyev ...................... 424/725 |
| 6,623,768 B1 | * | 9/2003 | Naguib .......................... 424/773 |
| 2003/0064937 A1 | * | 4/2003 | Nieuwenhuizen et al. ..... 514/27 |
| 2003/0103914 A1 | | 6/2003 | Lawlor |

FOREIGN PATENT DOCUMENTS

| | | | |
|---|---|---|---|
| CN | 1421240 | * | 6/2003 |
| CN | 1421240 A | * | 6/2003 |
| EP | 1 317 928 | | 6/2003 |
| FR | 2 571 257 | | 4/1986 |
| FR | 2571257 | * | 4/1986 |
| GB | 1 589 294 | | 5/1981 |
| JP | 06179609 A | * | 6/1994 |
| JP | 406179609 | * | 6/1994 |
| SU | 1373398 A | * | 2/1988 |
| WO | 97/41137 | | 11/1997 |

OTHER PUBLICATIONS

Giovanni et al (Oligomeric acylphloroglucinols from *Myrtle* (*Myrtle communis*), Journal of Natural Products, 65 (3): 334-8, 2002).*
Appendino et al., Oligomeric acylphloroglucinols from *Myrtle* (*Myrtle communis*), Journal of Natural Products, 65 (3): 334-8, 2002.*
Rosa et al, Antioxidant activity of oligomeric acylphloroglucinols from *Myrtus communis* L., Free radical research, (Sep. 2003) vol. 37, No. 9, pp. 1013-1019.*
Tagashira et al, Antioxidative activity of hop bitter acids and their analogues, Bioscience, biotechnology, and biochemistry, (Apr. 1995) vol. 59, No. 4, pp. 740-742.*
Tripathi et al, Antioxidant property of *Hypericum perforatum* (L.) of Indian origin and its comparison with established Medhya rasayanas [*Bacopa monnieri* and *Nardostachys jatamansi*] of Ayurvedic medicine, Current Science, (1999) vol. 76, No. 1, pp. 27-29.*
Mimica-Dukic et al, Antimicrobial and antioxidant activities of three *Mentha* species essential Oils, Planta medica, (May 2003) vol. 69, No. 5, pp. 413-419.*
Database WPI Section Ch, Week 199642 Derwent Publications Ltd., London, GB; Class B02, AN 1996-419777 XP002326320 & JP 08 20518 A (Nonogawa Shoji KK) Aug. 13, 1996 abstract.
Database WPI Section Ch, Week 199614 Derwent Publications Ltd., London, GB, Class B03, AN 1996-136189 XP002326321 & JP 08 027005 A (Pokka Corp KK) Jan. 30, 1996 abstract.
Database WPI Section Ch, Week 199650 Derwent Publications Ltd., London, GB CLass B04, AN 1996-502633 XP002326322 & JP 08 259452 A (Lotte Co Ltd) Oct. 8, 1996 abstract.

* cited by examiner

*Primary Examiner* — Qiuwen Mi
(74) *Attorney, Agent, or Firm* — Young & Thompson

(57) ABSTRACT

Compositions for the treatment of the affections of the oral cavity and upper respiratory tract include anthocyanosides, procyanidins and phloroglucinols. The anthocyanosides are derived from *Vaccinium myrtillus* extract, the procyanidins are derived from a *Vitus vinifera* extract, a *Camellia sinensis* extract or from other edible plants containing procyanidins, and the phloroglucinols are derived from *Hypericum* spp., *Myrtus* spp. or *Humulus lupulus* extracts.

18 Claims, No Drawings

COMPOSITIONS FOR THE TREATMENT OF AFFECTIONS OF THE ORAL CAVITY AND UPPER RESPIRATORY TRACT

BACKGROUND OF THE INVENTION

1. Field of the Invention

The present invention relates to compositions containing anthocyanosides and/or procyanidins in combination with floroglucinols for the treatment of the affections of the oral cavity and upper respiratory tract.

2. Description of the Related Art

Throat redness and inflammation, with formation of plaques, usually accompany common influenza, coryza and other cold diseases. Common cold and influenza, which on the average affect up to three times a year both children and adults, are related to mild viral infections caused by rhinovirus (40%), coronavirus (10%) and, to a less extent, adenovirus and parainfluenza viruses. Although no specific treatments exist for these pathologies, antihistamines and decongestants are considered useful, as the edema reduction alleviates pain and makes the course of the disease shorter.

SUMMARY OF THE INVENTION

The present invention relates to compositions containing:
a) anthocyanosides, and/or
b) procyanidins, and
c) floroglucinols,
useful for the treatment of the affections of the oral cavity and upper respiratory tract.

DETAILED DESCRIPTION OF THE PREFERRED EMBODIMENTS

According to the present invention, the compositions contain 1 to 200 mg of anthocyanosides, and/or 1 to 200 mg of procyanidans, and 1 to 200 mg of phloroglucinols.

According to the present invention, "anthocyanosides" includes both real anthocyanosides and anthocyanidins, their aglycones. The anthocyanosides preferably are derived from *Vaccinium myrtillus* extracts. The extract of bilberry (*Vaccinium myrtillus*), as described in literature, has marked anti-inflammatory activity, in particular topically, due to its action on capillary permeability and fragility. The preparation of bilberry extracts containing anthocyanosides is known to those skilled in the art. Bilberry anthocyanosides and procyanidins exert bacteriostatic action which prevents bacterial and fungal adhesion, for example at the dental and paradental level and on mucous membranes.

According to the present invention, the procyanidins can preferably be derived from *Vitis vinifera* extracts, obtained as disclosed in GB 1,541,469, or from *Camellia sinensis* extracts, as disclosed in EP 0 814 823, or from other plants, preferably edible, containing them.

Phloroglucinols exert strong bacteriostatic action on a great number of bacteria and fungi strains. The minimum inhibitor concentration values of some *phloroglucinols* on gram+ bacteria, gram- anaerobic bacteria and strains of *Candida albicans* range from 0.5 to 4 µg/ml.

According to the present invention, *phloroglucinols* can be derived from *Hypericum* spp. extracts, preferably *Hypericum perforatum*, or from *Myrtus* spp. extracts, preferably *Myrtus communis*, or from *Humulus* spp. fractions, preferably *Humulus lupulus*, enriched in α and β acids. According to the invention, the fraction of β-acids prepared from *Humulus lupulus* contains 20 to 80%, preferably 60%, of *phloroglucinols* expressed as colupulone; the fraction of α-acids contains 20 to 80%, preferably 60%, of humulone.

According to the present invention, among the *Hypericum* sp. extracts, particularly preferred is a *Hypericum perforatum* extract with a *phloroglucinols* (adhyperforin/hyperforin) content ranging from 20 to 80%, preferably 60%.

According to the present invention, the *Myrtus communis* extract is prepared from the leaves, by extraction with carbon dioxide under conditions of pressure ranging from 235 to 260 bars and temperature ranging from 40 to 60°C., preferably 45°C. The resulting extract usually has a *myrtucommulone* content of 35%.

The compositions of the invention are capable of preventing the formation of purulent plaques deriving from various saprophytic infections of the oral cavity, thus avoiding the use of antibiotics, while reducing the progress of the infection. In particular, the compositions of the invention proved to exert a synergistic effect mainly as regards the duration of the disease.

Furthermore, the compositions of the invention exert favourable action on the cleanliness of the oral cavity and the removal of the dental plaque, thanks to the effect reducing bacterial adhesiveness, as already mentioned, exerted by bilberry extract and procyanidins, and to the high activity of *phloroglucinols* on anaerobic bacterial strains.

The pharmaceutical compositions will be preferably presented in the form of tablets for the slow dissolution in the oral cavity or chewing gums which provide the slow release of the active principles. These compositions are used in preventive and prophylactic treatments as well as for the hygiene of the oral cavity.

According to a further preferred aspect, the compositions of the present invention will further contain essential oils, in particular mint oil.

According to a further preferred aspect, the compositions of the present invention will further contain a *Glycyrrhiza* extract, preferably having a content in glycyrrhizic acid of 10%.

The present invention, therefore, relates to compositions for the treatment of the affections of the oral cavity and upper respiratory tract, containing the combinations described above.

Said compositions will be prepared according to conventional methods well known in pharmaceutical technique, as those described in "Remington's Pharmaceutical Handbook", Mack Publishing Co., N.Y., USA, together with suitable excipients commonly used in the art.

The present invention also relates to the use of a combination of anthocyosides, and/or procyanosidins, and *phloglucinols*, for the preparation of a medicament for the treatment of the affections of the oral cavity and upper respiratory tract.

The examples reported hereinbelow further illustrate the invention.

EXAMPLE I

Tablets

| Each 500 mg tablet contains: | |
|---|---|
| *Vaccinium myrtillus* extract (25% in anthocyanidins) | 60 mg |
| *Humulus lupulus* extract (60% in floroglucinols) | 10 mg |
| Soy lecithin (30% phosphatidylcholine) | 30 mg |
| *Glycyrrhiza* extract (10% of glycyrrhizic acid) | 20 mg |

-continued

| Each 500 mg tablet contains: | |
|---|---|
| Mint essential oil | 10 mg |
| Saccharose | 200 mg |
| Maltodextrin | 150 mg |
| Acacia gum | 15 mg |
| Magnesium stearate | 5 mg |

EXAMPLE II

Tablets

| Each 500 mg tablet contains: | |
|---|---|
| *Vitis vinifera* extract (95% in procyanidins) | 80 mg |
| *Humulus lupulus* extract (60% in floroglucinols) | 10 mg |
| Soy lecithin (30% phosphatidylcholine) | 30 mg |
| *Glycyrrhiza* extract (10% of glycyrrhizic acid) | 20 mg |
| Mint essential oil | 10 mg |
| Mannitol | 320 mg |
| Povidone | 20 mg |
| Silicium dioxide | 5 mg |
| Magnesium stearate | 5 mg |

EXAMPLE III

Tablets

| Each 500 mg tablet contains: | |
|---|---|
| *Vitis vinifera* extract (95% in procyanidins) | 80 mg |
| *Myrtus communis* lipophilic extract (35% in mirtocupulone) | 10 mg |
| *Glycyrrhiza* extract (10% of glycyrrhizic acid) | 20 mg |
| Mint essential oil | 10 mg |
| Maltodextrin | 332 mg |
| Sodium saccharin | 3 mg |
| Arabic gum | 30 mg |
| Talc | 10 mg |
| Magnesium stearate | 5 mg |

EXAMPLE IV

Tablets

| Each 500 mg tablet contains: | |
|---|---|
| *Vaccinium myrtillus* extract (25% in anthocyanidins) | 60 mg |
| *Myrtus communis* lipophilic extract (35% in mirtocupulone) | 10 mg |
| Soy lecithin (30% phosphatidylcholine) | 30 mg |
| *Glycyrrhiza* extract (10% of glycyrrhizic acid) | 20 mg |
| Mint essential oil | 10 mg |
| Saccharose | 330 mg |
| Tragacanth gum | 20 mg |
| Silicium dioxide | 5 mg |
| Magnesium stearate | 5 mg |

EXAMPLE V

Tablets

| Each 500 mg tablet contains: | |
|---|---|
| *Camellia sinensis* extract (70% in procyanidole oligomers) | 80 mg |
| *Humulus lupulus* extract (60% in floroglucinols) | 10 mg |
| Soy lecithin (30% phosphatidylcholine) | 30 mg |
| *Glycyrrhiza* extract (10% of glycyrrhizic acid) | 20 mg |
| Mint essential oil | 10 mg |
| Mannitol | 320 mg |
| Povidone | 20 mg |
| Silicium dioxide | 5 mg |
| Magnesium stearate | 5 mg |

EXAMPLE VI

Tablets

| Each 500 mg tablet contains: | |
|---|---|
| *Camellia sinensis* extract (70% in procyanidole oligomers) | 80 mg |
| *Hypericum perforatum* extract (60% in floroglucinols) | 10 mg |
| Soy lecithin (30% phosphatidylcholine) | 30 mg |
| *Glycyrrhiza* extract (10% of glycyrrhizic acid) | 20 mg |
| Mint essential oil | 10 mg |
| Mannitol | 320 mg |
| Povidone | 20 mg |
| Silicium dioxide | 5 mg |
| Magnesium stearate | 5 mg |

EXAMPLE VII

Chewing Gum

| Each 2000 mg chewing gum contains: | |
|---|---|
| *Vitis vinifera* extract (95% in procyanidins) | 80 mg |
| *Myrtus communis* lipophilic extract (30% in mirtocupulone) | 10 mg |
| *Glycyrrhiza* extract (10% of glycyrrhizic acid) | 20 mg |
| Mint essential oil | 10 mg |
| Gum base | 1598 mg |
| Xylitol | 250 mg |
| Aspartame | 2 mg |
| Magnesium stearate | 15 mg |
| Talc | 15 mg |

The invention claimed is:

1. A composition, for the treatment of an affection of the oral cavity and upper respiratory tract, comprising:
   1-200 mg anthocyanosides;
   1-200 mg procyanidins; and
   1-200 mg phloroglucinols,
   Wherein the anthocyanosides are derived from a *Vaccinium myrtillus* extract, the procyanidins are derived from a *Vitis vinifera* extract, a *Camellia sinensis* extract or from another edible plant containing the procyanidins, and the phloroglucinols are derived from *Hypericum* spp., *Myrtus* spp. or *Humulus lupulus* extracts.

2. The composition as claimed in claim 1, wherein the phloroglucinols are derived from *Hypericum perforatum* or

*Myrtus communis* extracts, or from *Humulus lupulus* fractions enriched in α and β acids.

3. The composition as claimed in claim 2, wherein 20-80% of the phloroglucinols from the β acids of *Humulus lupulus* are colupulone, and the α acids contain 20-80% of humulone.

4. The composition as claimed in claim 3, wherein 60% of the phloroglucinols from the β acids of *Humulus lupulus* are colupulone, and the α acids contain 60% of humulone.

5. The composition as claimed in claim 1, wherein the *Hypericum sp* extract is a *Hypericum perforatum* extract with a phloroglucinol content ranging from 20-80%.

6. The composition as claimed in claim 5, wherein the phloroglucinols content of the Hypericum perforatum extract is 60%.

7. The composition as claimed in claim 2, wherein the *Myrtus communis* extract is prepared from leaves of *Myrtus communis* by extraction with carbon dioxide at a pressure ranging from 235 to 260 bars and a temperature ranging from 40-60° C.

8. The composition as claimed in claim 7, wherein the *Myrtus communis* extract has a myrtucommulone content of 35%.

9. The composition as claimed in claim 1, further containing at least one essential oil.

10. The composition as claimed in claim 9, wherein the essential oil is mint oil.

11. A method for the treatment of an affection of the oral cavity and upper respiratory tract, said method comprises: administering to a patient in need thereof an effective amount of a medicament containing:
    1-200 mg anthocyanosides;
    1-200 mg procyanidins; and
    1-200 mg phloroglucinols,
    Wherein the anthocyanosides are derived from a *Vaccinium myrtillus* extract, the procyanidins are derived from a *Vitis vinifera* extract, a *Camellia sinensis* extract or from another edible plant containing the procyanidins, and the phloroglucinols are derived from *Hypericum* spp., *Myrtus* spp. or *Humulus lupulus* extracts.

12. The method as claimed in claim 11, wherein the phloroglucinols are derived from *Hypericum perforatum* or *Myrtus communis* extracts, or from *Humulus lupulus* fractions enriched in α and β acids.

13. The method as claimed in claim 12, wherein 20-80% of the phloroglucinols from the β acids of *Humulus lupulus* are colupulone, and the α acids contain 20-80% of humulone.

14. The method as claimed in claim 13, wherein 60% of the phloroglucinols from the β acids of *Humulus lupulus* are colupulone, and the α acids contain 60% of humulone.

15. The method as claimed in claim 11, wherein the *Hypericum* sp extract is a *Hypericum perforatum* extract with a phloroglucinol content ranging from 20-80%.

16. The method as claimed in claim 15, wherein the phloroglucinols content of the *Hypericum perforatum* extract is 60%.

17. The method as claimed in claim 12, wherein the *Myrtus communis* extract is prepared from leaves of *Myrtus communis* by extraction with carbon dioxide at a pressure ranging from 235 to 260 bars and a temperature ranging from 40-60° C.

18. The method as claimed in claim 12, wherein the *Myrtus communis* extract has a myrtucommulone content of 35%.

* * * * *